United States Patent
Nash et al.

(10) Patent No.: US 9,872,718 B2
(45) Date of Patent: *Jan. 23, 2018

(54) SHAFTS WITH PRESSURE RELIEF IN CRYOTHERAPEUTIC CATHETERS AND ASSOCIATED DEVICES, SYSTEMS, AND METHODS

(71) Applicant: Medtronic Ardian Luxembourg S.a.r.l., Luxembourg (LU)

(72) Inventors: Stephen Nash, Ballybrit (IE); Grace Kelly, Ballybrit (IE)

(73) Assignee: Medtronic Adrian Luxembourg S.a.r.l., Luxembourg (LU)

(*) Notice: Subject to any disclaimer, the term of this patent is extended or adjusted under 35 U.S.C. 154(b) by 0 days.

This patent is subject to a terminal disclaimer.

(21) Appl. No.: 14/967,425

(22) Filed: Dec. 14, 2015

(65) Prior Publication Data
US 2016/0166305 A1 Jun. 16, 2016

Related U.S. Application Data

(63) Continuation of application No. 13/458,120, filed on Apr. 27, 2012, now Pat. No. 9,241,752.

(51) Int. Cl.
*A61B 18/02* (2006.01)
*A61M 25/10* (2013.01)
(Continued)

(52) U.S. Cl.
CPC ......... *A61B 18/02* (2013.01); *A61M 25/1006* (2013.01); *A61M 25/1025* (2013.01);
(Continued)

(58) Field of Classification Search
CPC ........ A61M 25/1018; A61M 25/10184; A61M 25/10185; A61M 25/10186;
(Continued)

(56) References Cited

U.S. PATENT DOCUMENTS 3,125,096 A 3/1964 Antiles et al.
3,298,371 A 1/1967 Lee
(Continued)

FOREIGN PATENT DOCUMENTS

CN 1408451 4/2003
DE 4406451 9/1995
(Continued)

OTHER PUBLICATIONS

U.S. Appl. No. 95/002,110, filed Aug. 29, 2012, Demarais et al.
(Continued)

*Primary Examiner* — Eugene T Wu

(57) ABSTRACT

Cryotherapeutic systems with features that can facilitate pressure relief in the event of exhaust-passage blockage and associated devices, systems, and methods are disclosed herein. A cryotherapeutic system configured in accordance with a particular embodiment can include an elongated shaft having a distal portion and a pressure-relief portion proximal to the distal portion. The cryotherapeutic system can further include a supply lumen, an exhaust passage, and a balloon configured to receive refrigerant from the supply lumen and to exhaust refrigerant to the exhaust passage. The pressure-relief portion can be configured to release refrigerant from the exhaust passage when a pressure of refrigerant in the exhaust passage exceeds a threshold pressure less than a pressure rating of the balloon. The pressure-relief portion, for example, can include a rupture element configured to rupture at about the threshold pressure.

15 Claims, 6 Drawing Sheets

(51) Int. Cl.
*A61B 18/00* (2006.01)
*A61B 90/00* (2016.01)

(52) U.S. Cl.
CPC ........ *A61M 25/10184* (2013.11); *A61B 90/03* (2016.02); *A61B 2018/00005* (2013.01); *A61B 2018/0022* (2013.01); *A61B 2018/00023* (2013.01); *A61B 2018/00166* (2013.01); *A61B 2018/0212* (2013.01); *A61B 2018/0262* (2013.01); *A61B 2018/0268* (2013.01); *A61B 2090/032* (2016.02); *A61B 2090/037* (2016.02); *A61M 2025/1061* (2013.01); *F04C 2270/041* (2013.01)

(58) Field of Classification Search
CPC .......... A61M 25/1025; A61M 25/1036; A61M 2025/1059; A61M 2025/1061; A61M 2025/1034; A61M 2025/0029; A61M 2025/003; A61M 2025/0034; A61B 18/02; A61B 2018/0212; A61B 2018/0231; A61B 2018/0262; A61B 2018/00005; A61B 2018/00011; A61B 2018/00017; A61B 2018/00023; F16K 17/00; F16K 17/003; F16K 17/02; F16K 17/025; F16K 17/14; F16K 17/16; F16K 17/1606; F16K 17/1613; F16K 17/162; F16K 17/1626; F16K 17/1633; F16K 17/20; F16K 17/22; F16K 17/24; F16K 17/28; F16K 17/40; F16K 17/403
See application file for complete search history.

(56) References Cited

U.S. PATENT DOCUMENTS

| | | | |
|---|---|---|---|
| 3,901,241 A | 8/1975 | Allen, Jr. | |
| 3,924,628 A | 12/1975 | Droegemueller et al. | |
| 4,143,651 A * | 3/1979 | Patel | A61M 25/10 604/100.01 |
| 4,275,734 A | 6/1981 | Mitchiner | |
| 4,483,341 A | 11/1984 | Witteles | |
| 4,602,624 A | 7/1986 | Naples et al. | |
| 4,649,936 A | 3/1987 | Ungar et al. | |
| 4,709,698 A | 12/1987 | Johnston et al. | |
| 4,764,504 A | 8/1988 | Johnson et al. | |
| 4,890,623 A | 1/1990 | Cook et al. | |
| 4,976,711 A | 12/1990 | Parins et al. | |
| 5,108,390 A | 4/1992 | Potocky et al. | |
| 5,190,539 A | 3/1993 | Fletcher et al. | |
| 5,300,068 A | 4/1994 | Rosar et al. | |
| 5,308,323 A | 5/1994 | Sogawa et al. | |
| 5,334,181 A | 8/1994 | Rubinsky et al. | |
| 5,342,301 A | 8/1994 | Saab | |
| 5,358,514 A | 10/1994 | Schulman et al. | |
| 5,368,591 A | 11/1994 | Lennox et al. | |
| 5,383,856 A | 1/1995 | Bersin | |
| 5,417,355 A | 5/1995 | Broussalian et al. | |
| 5,423,744 A | 6/1995 | Gencheff et al. | |
| 5,425,364 A | 6/1995 | Imran | |
| 5,484,400 A | 1/1996 | Edwards et al. | |
| 5,571,147 A | 11/1996 | Sluijter et al. | |
| 5,588,964 A | 12/1996 | Imran et al. | |
| 5,599,345 A | 2/1997 | Edwards et al. | |
| 5,624,392 A | 4/1997 | Saab | |
| 5,626,576 A | 5/1997 | Janssen | |
| 5,672,174 A | 9/1997 | Gough et al. | |
| 5,688,266 A | 11/1997 | Edwards et al. | |
| 5,700,282 A | 12/1997 | Zabara | |
| 5,707,400 A | 1/1998 | Terry, Jr. et al. | |
| 5,758,505 A | 6/1998 | Dobak, III et al. | |
| 5,772,590 A | 6/1998 | Webster, Jr. | |
| 5,807,391 A | 9/1998 | Wijkamp | |
| 5,837,003 A | 11/1998 | Ginsburg | |
| 5,860,970 A | 1/1999 | Goddard et al. | |
| 5,860,974 A | 1/1999 | Abele | |
| 5,865,787 A | 2/1999 | Shapland et al. | |
| 5,868,735 A | 2/1999 | Lafontaine | |
| 5,893,885 A | 4/1999 | Webster et al. | |
| 5,902,299 A | 5/1999 | Jayaraman | |
| 5,944,710 A | 8/1999 | Dev et al. | |
| 5,954,719 A | 9/1999 | Chen et al. | |
| 5,971,979 A | 10/1999 | Joye et al. | |
| 5,983,141 A | 11/1999 | Sluijter et al. | |
| 6,004,269 A | 12/1999 | Crowley et al. | |
| 6,009,877 A | 1/2000 | Edwards | |
| 6,012,457 A | 1/2000 | Lesh | |
| 6,024,740 A | 2/2000 | Lesh et al. | |
| 6,024,752 A | 2/2000 | Horn et al. | |
| 6,032,675 A | 3/2000 | Rubinsky | |
| 6,036,687 A | 3/2000 | Laufer et al. | |
| 6,056,744 A | 5/2000 | Edwards | |
| 6,066,134 A | 5/2000 | Eggers et al. | |
| 6,091,995 A | 7/2000 | Ingle et al. | |
| 6,099,524 A | 8/2000 | Lipson et al. | |
| 6,117,101 A | 9/2000 | Diederich et al. | |
| 6,135,999 A | 10/2000 | Fanton et al. | |
| 6,142,991 A | 11/2000 | Schatzberger | |
| 6,142,993 A | 11/2000 | Whayne et al. | |
| 6,149,620 A | 11/2000 | Baker et al. | |
| 6,161,048 A | 12/2000 | Sluijter et al. | |
| 6,161,049 A | 12/2000 | Rudie et al. | |
| 6,161,543 A | 12/2000 | Cox et al. | |
| 6,164,283 A | 12/2000 | Lesh | |
| 6,190,356 B1 | 2/2001 | Bersin | |
| 6,219,577 B1 | 4/2001 | Brown, III et al. | |
| 6,224,592 B1 | 5/2001 | Eggers et al. | |
| 6,237,355 B1 | 5/2001 | Li | |
| 6,241,722 B1 | 6/2001 | Dobak et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,283,959 B1 | 9/2001 | Lalonde et al. | |
| 6,290,696 B1 | 9/2001 | Lafontaine | |
| 6,292,695 B1 | 9/2001 | Webster, Jr. et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,355,029 B1 | 3/2002 | Joye et al. | |
| 6,405,732 B1 | 6/2002 | Edwards et al. | |
| 6,413,255 B1 | 7/2002 | Stern | |
| 6,428,534 B1 | 8/2002 | Joye et al. | |
| 6,432,102 B2 | 8/2002 | Joye et al. | |
| 6,451,045 B1 | 9/2002 | Walker et al. | |
| 6,468,297 B1 | 10/2002 | Williams et al. | |
| 6,488,679 B1 | 12/2002 | Swanson et al. | |
| 6,496,737 B2 | 12/2002 | Rudie et al. | |
| 6,497,703 B1 | 12/2002 | Korteling et al. | |
| 6,506,189 B1 | 1/2003 | Rittman, III et al. | |
| 6,514,226 B1 | 2/2003 | Levin et al. | |
| 6,514,245 B1 | 2/2003 | Williams et al. | |
| 6,517,533 B1 | 2/2003 | Swaminathan | |
| 6,522,926 B1 | 2/2003 | Kieval et al. | |
| 6,527,739 B1 | 3/2003 | Bigus et al. | |
| 6,527,765 B2 | 3/2003 | Kelman et al. | |
| 6,537,271 B1 | 3/2003 | Murray et al. | |
| 6,540,734 B1 | 4/2003 | Chiu et al. | |
| 6,542,781 B1 | 4/2003 | Koblish et al. | |
| 6,551,309 B1 | 4/2003 | LePivert | |
| 6,562,034 B2 | 5/2003 | Edwards et al. | |
| 6,575,933 B1 | 6/2003 | Wittenberger et al. | |
| 6,602,246 B1 | 8/2003 | Joye et al. | |
| 6,602,247 B2 | 8/2003 | Lalonde | |
| 6,610,083 B2 | 8/2003 | Keller et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,640,120 B1 | 10/2003 | Swanson et al. | |
| 6,648,878 B2 | 11/2003 | Lafontaine | |
| 6,648,879 B2 | 11/2003 | Joye et al. | |
| 6,666,858 B2 | 12/2003 | Lafontaine | |
| 6,673,066 B2 | 1/2004 | Werneth | |
| 6,685,648 B2 | 2/2004 | Flaherty et al. | |

(56) References Cited

U.S. PATENT DOCUMENTS

| | | |
|---|---|---|
| 6,685,732 B2 | 2/2004 | Kramer |
| 6,706,037 B2 | 3/2004 | Zvuloni et al. |
| 6,709,431 B2 | 3/2004 | Lafontaine |
| 6,711,444 B2 | 3/2004 | Koblish |
| 6,736,835 B2 | 5/2004 | Pellegrino et al. |
| 6,752,805 B2 | 6/2004 | Maguire et al. |
| 6,755,823 B2 | 6/2004 | Lalonde |
| 6,786,900 B2 | 9/2004 | Joye et al. |
| 6,786,901 B2 | 9/2004 | Joye et al. |
| 6,807,444 B2 | 10/2004 | Tu et al. |
| 6,811,550 B2 | 11/2004 | Holland et al. |
| 6,824,543 B2 | 11/2004 | Lentz |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,875,209 B2 | 4/2005 | Zvuloni et al. |
| 6,885,888 B2 | 4/2005 | Rezai |
| 6,893,436 B2 | 5/2005 | Woodard et al. |
| 6,905,510 B2 | 6/2005 | Saab |
| 6,908,462 B2 | 6/2005 | Joye et al. |
| 6,923,808 B2 | 8/2005 | Taimisto |
| 6,929,639 B2 | 8/2005 | Lafontaine |
| 6,939,346 B2 | 9/2005 | Kannenberg et al. |
| 6,955,174 B2 | 10/2005 | Joye et al. |
| 6,972,015 B2 | 12/2005 | Joye et al. |
| 6,981,382 B2 | 1/2006 | Lentz et al. |
| 6,989,009 B2 | 1/2006 | Lafontaine |
| 7,001,378 B2 | 2/2006 | Yon et al. |
| 7,022,120 B2 | 4/2006 | Lafontaine |
| 7,060,062 B2 | 6/2006 | Joye et al. |
| 7,081,112 B2 | 7/2006 | Joye et al. |
| 7,081,115 B2 | 7/2006 | Taimisto |
| 7,101,368 B2 | 9/2006 | Lafontaine |
| 7,149,574 B2 | 12/2006 | Yun et al. |
| 7,156,840 B2 | 1/2007 | Lentz et al. |
| 7,162,303 B2 | 1/2007 | Levin et al. |
| 7,172,589 B2 | 2/2007 | Lafontaine |
| 7,189,227 B2 | 3/2007 | Lafontaine |
| 7,221,979 B2 | 5/2007 | Zhou et al. |
| 7,288,089 B2 | 10/2007 | Yon et al. |
| 7,300,433 B2 | 11/2007 | Lane et al. |
| 7,306,590 B2 | 12/2007 | Swanson |
| 7,357,797 B2 | 4/2008 | Ryba |
| 7,381,200 B2 | 6/2008 | Katoh et al. |
| 7,387,126 B2 | 6/2008 | Cox et al. |
| 7,390,894 B2 | 6/2008 | Weinshilboum et al. |
| 7,449,018 B2 | 11/2008 | Kramer |
| 7,487,780 B2 | 2/2009 | Hooven |
| 7,507,233 B2 | 3/2009 | Littrup et al. |
| 7,556,624 B2 | 7/2009 | Laufer et al. |
| 7,604,631 B2 | 10/2009 | Reynolds |
| 7,617,005 B2 | 11/2009 | Demarais et al. |
| 7,620,451 B2 | 11/2009 | Demarais et al. |
| 7,641,679 B2 | 1/2010 | Joye et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,727,191 B2 | 6/2010 | Mihalik et al. |
| 7,758,571 B2 | 7/2010 | Saadat |
| 7,778,703 B2 | 8/2010 | Gross et al. |
| 7,785,289 B2 | 8/2010 | Rios et al. |
| 7,861,725 B2 | 1/2011 | Swanson |
| 7,892,201 B1* | 2/2011 | Laguna ............... A61M 25/10 604/96.01 |
| 7,947,014 B2* | 5/2011 | Kien ................ A61M 25/1018 604/118 |
| 7,972,327 B2 | 7/2011 | Eberl et al. |
| 8,012,147 B2 | 9/2011 | Lafontaine |
| 8,062,289 B2 | 11/2011 | Babaev |
| 8,080,006 B2 | 12/2011 | Lafontaine et al. |
| 8,088,125 B2 | 1/2012 | Lafontaine |
| 8,123,741 B2 | 2/2012 | Marrouche et al. |
| 8,128,617 B2 | 3/2012 | Bencini et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,261 B2 | 5/2012 | Watson |
| 8,439,909 B2 | 5/2013 | Wang et al. |
| 8,469,919 B2 | 6/2013 | Ingle et al. |
| 8,473,067 B2 | 6/2013 | Hastings et al. |
| 8,475,441 B2 | 7/2013 | Babkin et al. |
| 8,480,663 B2 | 7/2013 | Ingle et al. |
| 8,480,664 B2 | 7/2013 | Watson et al. |
| 8,663,211 B2 | 3/2014 | Fourkas et al. |
| 8,740,895 B2 | 6/2014 | Mayse et al. |
| 8,777,943 B2 | 7/2014 | Mayse |
| 8,814,899 B2* | 8/2014 | Pepper ............... A61M 25/0075 604/237 |
| 9,101,343 B2 | 8/2015 | Duong et al. |
| 9,259,559 B2* | 2/2016 | Pepper ................. A61M 29/02 |
| 2002/0045893 A1 | 4/2002 | Lane et al. |
| 2002/0045894 A1* | 4/2002 | Joye ...................... A61B 18/02 606/21 |
| 2002/0065487 A1 | 5/2002 | Wollschlager |
| 2002/0087208 A1 | 7/2002 | Koblish et al. |
| 2002/0107515 A1 | 8/2002 | Edwards et al. |
| 2002/0120258 A1 | 8/2002 | Lalonde |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0014095 A1 | 1/2003 | Kramer et al. |
| 2003/0036752 A1 | 2/2003 | Joye et al. |
| 2003/0050635 A1 | 3/2003 | Truckai et al. |
| 2003/0050681 A1 | 3/2003 | Pianca et al. |
| 2003/0060762 A1* | 3/2003 | Zvuloni ............... A61B 18/02 604/113 |
| 2003/0060858 A1 | 3/2003 | Kieval et al. |
| 2003/0074039 A1 | 4/2003 | Puskas |
| 2003/0088189 A1 | 5/2003 | Tu et al. |
| 2003/0088208 A1 | 5/2003 | Saadat |
| 2003/0109912 A1* | 6/2003 | Joye ...................... A61B 18/02 607/113 |
| 2003/0125721 A1* | 7/2003 | Yon ..................... A61B 18/02 606/21 |
| 2003/0125790 A1 | 7/2003 | Fastovsky et al. |
| 2003/0181897 A1 | 9/2003 | Thomas et al. |
| 2003/0195507 A1 | 10/2003 | Stewart et al. |
| 2003/0199861 A1* | 10/2003 | Lafontaine ............ A61B 18/02 606/21 |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danek et al. |
| 2004/0010289 A1 | 1/2004 | Biggs et al. |
| 2004/0024392 A1 | 2/2004 | Lewis et al. |
| 2004/0167509 A1 | 8/2004 | Taimisto |
| 2004/0215186 A1 | 10/2004 | Cornelius et al. |
| 2004/0243119 A1 | 12/2004 | Lane et al. |
| 2004/0267250 A1 | 12/2004 | Yon et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0209587 A1 | 9/2005 | Joye et al. |
| 2005/0228367 A1* | 10/2005 | Abboud ................ A61B 18/02 606/20 |
| 2005/0228460 A1 | 10/2005 | Levin et al. |
| 2005/0240117 A1 | 10/2005 | Zvuloni et al. |
| 2006/0084962 A1* | 4/2006 | Joye ...................... A61B 18/02 606/21 |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0161102 A1* | 7/2006 | Newcomb ......... A61M 25/0097 604/96.01 |
| 2006/0167438 A1* | 7/2006 | Kalser ................. A61B 5/205 604/544 |
| 2006/0206150 A1 | 9/2006 | Demarais et al. |
| 2006/0212027 A1 | 9/2006 | Marrouche et al. |

(56) References Cited

U.S. PATENT DOCUMENTS

| | | |
|---|---|---|
| 2006/0212076 A1 | 9/2006 | Demarais et al. |
| 2006/0247611 A1 | 11/2006 | Abboud et al. |
| 2006/0264823 A1* | 11/2006 | Newcomb ......... A61M 25/0097 604/99.01 |
| 2006/0270982 A1* | 11/2006 | Mihalik ................ A61B 18/02 604/113 |
| 2006/0271111 A1 | 11/2006 | Demarais et al. |
| 2007/0049924 A1 | 3/2007 | Rahn |
| 2007/0093710 A1 | 4/2007 | Maschke |
| 2007/0129720 A1 | 6/2007 | Demarais et al. |
| 2007/0185445 A1 | 8/2007 | Nahon et al. |
| 2007/0265687 A1 | 11/2007 | Deem et al. |
| 2007/0299433 A1 | 12/2007 | Williams et al. |
| 2008/0097251 A1 | 4/2008 | Babaev |
| 2008/0171974 A1 | 7/2008 | Lafontaine et al. |
| 2008/0208182 A1 | 8/2008 | Lafontaine et al. |
| 2008/0300584 A1 | 12/2008 | Lentz et al. |
| 2008/0306475 A1 | 12/2008 | Lentz et al. |
| 2008/0312644 A1 | 12/2008 | Fourkas et al. |
| 2008/0319513 A1 | 12/2008 | Pu et al. |
| 2009/0036948 A1 | 2/2009 | Levin et al. |
| 2009/0171333 A1 | 7/2009 | Hon |
| 2009/0182316 A1 | 7/2009 | Bencini |
| 2009/0182317 A1 | 7/2009 | Bencini |
| 2009/0209949 A1 | 8/2009 | Ingle et al. |
| 2009/0221955 A1 | 9/2009 | Babaev |
| 2009/0281533 A1 | 11/2009 | Ingle et al. |
| 2009/0287202 A1 | 11/2009 | Ingle et al. |
| 2009/0299355 A1 | 12/2009 | Bencini et al. |
| 2010/0049184 A1 | 2/2010 | George et al. |
| 2010/0069900 A1* | 3/2010 | Shirley ................ A61B 18/02 606/21 |
| 2010/0100087 A1 | 4/2010 | Mazzone et al. |
| 2010/0106148 A1 | 4/2010 | Joye et al. |
| 2010/0114269 A1 | 5/2010 | Wittenberger et al. |
| 2010/0125266 A1 | 5/2010 | Deem et al. |
| 2010/0130970 A1 | 5/2010 | Williams et al. |
| 2010/0137860 A1 | 6/2010 | Demarais et al. |
| 2010/0137952 A1 | 6/2010 | Demarais et al. |
| 2010/0179526 A1 | 7/2010 | Lawrence |
| 2010/0179527 A1 | 7/2010 | Watson et al. |
| 2010/0191112 A1 | 7/2010 | Demarais et al. |
| 2010/0198203 A1 | 8/2010 | Kuck et al. |
| 2010/0217189 A1* | 8/2010 | Pepper ............... A61M 25/0075 604/99.04 |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0234838 A1 | 9/2010 | Watson |
| 2010/0249766 A1 | 9/2010 | Saadat |
| 2010/0256621 A1 | 10/2010 | Babkin et al. |
| 2010/0274189 A1* | 10/2010 | Kurth ................ A61M 25/1006 604/103.1 |
| 2010/0280507 A1 | 11/2010 | Babkin et al. |
| 2010/0292640 A1* | 11/2010 | Kien ................ A61M 25/1018 604/99.02 |
| 2011/0125143 A1 | 5/2011 | Gross et al. |
| 2011/0152855 A1 | 6/2011 | Mayse et al. |
| 2011/0257642 A1 | 10/2011 | Griggs, III |
| 2011/0263921 A1 | 10/2011 | Vrba et al. |
| 2011/0270238 A1 | 11/2011 | Rizq et al. |
| 2011/0282272 A1 | 11/2011 | Lafontaine |
| 2012/0029509 A1 | 2/2012 | Smith |
| 2012/0029511 A1 | 2/2012 | Smith et al. |
| 2012/0089047 A1 | 4/2012 | Ryba et al. |
| 2012/0109021 A1 | 5/2012 | Hastings et al. |
| 2012/0123261 A1 | 5/2012 | Jenson et al. |
| 2012/0130289 A1 | 5/2012 | Demarais et al. |
| 2012/0130345 A1 | 5/2012 | Levin et al. |
| 2012/0130360 A1 | 5/2012 | Buckley et al. |
| 2012/0130368 A1 | 5/2012 | Jenson |
| 2012/0136417 A1 | 5/2012 | Buckley et al. |
| 2012/0136418 A1 | 5/2012 | Buckley et al. |
| 2012/0143097 A1 | 6/2012 | Pike, Jr. |
| 2012/0143177 A1 | 6/2012 | Avitall |
| 2012/0150267 A1 | 6/2012 | Buckley et al. |
| 2012/0172837 A1 | 7/2012 | Demarais et al. |
| 2012/0253336 A1 | 10/2012 | Littrup et al. |
| 2013/0090650 A1 | 4/2013 | Jenson et al. |
| 2013/0123770 A1 | 5/2013 | Smith |
| 2013/0184696 A1 | 7/2013 | Fourkas et al. |
| 2013/0345688 A1 | 12/2013 | Babkin et al. |
| 2014/0046313 A1 | 2/2014 | Pederson et al. |
| 2014/0066914 A1 | 3/2014 | Lafontaine |
| 2014/0276724 A1 | 9/2014 | Goshayeshgar |
| 2014/0276728 A1 | 9/2014 | Goshayeshgar |
| 2014/0276811 A1 | 9/2014 | Koblish et al. |
| 2014/0364893 A1* | 12/2014 | Pepper ............... A61M 25/0075 606/192 |
| 2015/0105764 A1 | 4/2015 | Rizq et al. |
| 2015/0231378 A1* | 8/2015 | Pepper ................. A61M 29/02 606/194 |

FOREIGN PATENT DOCUMENTS

| | | |
|---|---|---|
| DE | 102005041601 | 4/2007 |
| EP | 0655225 | 5/1995 |
| EP | 0955012 | 11/1999 |
| EP | 1129670 | 9/2001 |
| EP | 1164963 | 1/2002 |
| EP | 1210959 | 6/2002 |
| EP | 1389477 | 2/2004 |
| EP | 1502553 | 2/2005 |
| EP | 1559362 | 8/2005 |
| EP | 2558016 | 2/2013 |
| EP | 2598070 | 6/2013 |
| EP | 2598071 | 6/2013 |
| EP | 2608837 | 7/2013 |
| GB | 1422535 | 1/1976 |
| GB | 2283678 | 5/1995 |
| GB | 2289414 | 11/1995 |
| SU | 718099 | 2/1980 |
| SU | 1153901 | 5/1985 |
| SU | 1329781 | 8/1987 |
| SU | 1378835 | 3/1988 |
| SU | 1771725 | 10/1992 |
| WO | WO-199407446 | 4/1994 |
| WO | WO-1995025472 | 9/1995 |
| WO | WO-9531142 | 11/1995 |
| WO | WO-9725011 | 7/1997 |
| WO | WO-1997036548 | 10/1997 |
| WO | WO1998042403 | 10/1998 |
| WO | WO-9900060 | 1/1999 |
| WO | WO-9905979 | 2/1999 |
| WO | WO-9927862 | 6/1999 |
| WO | WO-0047118 | 8/2000 |
| WO | WO-2001022897 | 4/2001 |
| WO | WO-0164145 | 9/2001 |
| WO | WO-2001070114 | 9/2001 |
| WO | WO-0200128 | 1/2002 |
| WO | WO-0204042 | 1/2002 |
| WO | WO-0207625 | 1/2002 |
| WO | WO-0207628 | 1/2002 |
| WO | WO-0213710 | 2/2002 |
| WO | WO-0215807 | 2/2002 |
| WO | WO-02058576 | 8/2002 |
| WO | WO-03020334 | 3/2003 |
| WO | WO-2003022167 | 3/2003 |
| WO | WO-03061496 | 7/2003 |
| WO | WO-2003/082080 | 10/2003 |
| WO | WO-2005030072 | 4/2005 |
| WO | WO-2005038357 | 4/2005 |
| WO | WO--2005041748 | 5/2005 |
| WO | WO-2005/110528 | 11/2005 |
| WO | WO-2006041881 | 4/2006 |
| WO | WO-2006096272 | 9/2006 |
| WO | WO-2006105121 | 10/2006 |
| WO | WO-2006124177 | 11/2006 |
| WO | WO-2007008954 | 1/2007 |
| WO | WO-2007078997 | 7/2007 |
| WO | WO-2008049084 | 4/2008 |
| WO | WO-2008131037 | 10/2008 |
| WO | WO-2011056684 | 5/2011 |

(56) References Cited

FOREIGN PATENT DOCUMENTS

| WO | WO-2011082278 | 7/2011 |
|---|---|---|
| WO | WO-2011082279 | 7/2011 |
| WO | WO-2012016135 | 2/2012 |
| WO | WO-2012016137 | 2/2012 |
| WO | WO-2012058430 | 5/2012 |
| WO | WO-2013074683 | 5/2013 |
| WO | WO-2013106859 | 7/2013 |
| WO | WO-2013163325 | 10/2013 |
| WO | WO-2014/150204 | 9/2014 |
| WO | WO-2014/158727 | 10/2014 |
| WO | WO-2014/164445 | 10/2014 |

OTHER PUBLICATIONS

U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty For The Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al. "Feasibility of cardiac cryoablation using a transvenous steerable electrode catheter." J Intery Cardiac Electrophysiol, 2:285-292 (1998).
Final Office Action, U.S. Appl. No. 12/827,700, dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.

(56) References Cited

OTHER PUBLICATIONS

Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding A Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

(56) References Cited

OTHER PUBLICATIONS

Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
International Search Report and Written Opinion of International Application No. PCT/US2013/038036, dated Jan. 15, 2014, 24 pages.

European Search Report for European Application No. 13159256, dated Oct. 17, 2013, 6 pages.
510K Summary of CryoGen Cryosurgery System, filed with FDA Jul. 3, 1997—approved Oct. 1, 1997, 1997, 5 pages.
CO2/Gas Composite Regulator, Sep. 6, 2011, 2 pages. <http://www.genuineinnovations.com/composite-regulator.html>.
CryoGen SS&E: HerOption Uterine Cryoblatin Therapy System, filed with FDA Aug. 15, 2000 approved Apr. 20, 2001, 1999, 84 pages.
International Search Report and Written Opinion for International Application No. PCT/US2012/063411 dated Jun. 13, 2013, 13 pages.
Lura Harrison, Ph.D. et al., "Cryosurgical Ablation of the A-V Node-His Bundle—A New Method for Producing A-V Block," Circulation, vol. 55, 1977 pp. 463-470.
Medical Grade Gas Dispenser, Sep. 6, 2011, 1 page, <http://www.abd-inc.com/Frame-904990-page1namepage904990.html?refresh=1205442262133>.
Sesia G. et al., "The use of nitrous oxide as a freezing agent in cryosurgery of the prostate," International Surgery [Int Surg], vol. 53, 1970, pp. 82-90.
Special Order Only Thermal Dilution Injector, Obsolete Product, Sep. 6, 2011, 1 page, <http://www.abd-inc.com/Frame-904990-page1namepage904990.html?refresh=1205442262133>.
Torre, Douglas, MD, "Alternate Cryogens for Cryosurgery," J. Derm. Surgery, Jun. 1975, pp. 56-58.
Voĭ tyna SV, "Cryocatheter-tourniquet," Meditsinskaia Tekhnika [Med Tekh], vol. 6, 1976, pp. 47-48.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.com/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper et al., "Design and Implementation of a New Computerized System for Intraoperative Cardiac Mapping." Journal of Applied Physiology, 1991, vol. 71, No. 4, pp. 1529-1539.

(56) References Cited

OTHER PUBLICATIONS

Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 60/852,787, filed Oct. 18, 2006, 112 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Doumas, et al., "Renal Nerve Ablation for Resistant Hypertension: The Dust Has Not Yet Settled." The Journal of Clinical Hypertension. 2014; vol. 16, No. 6, 2 pages.
Opposition to European Patent No. 2,465,470, Granted Oct. 28, 2015, Date of Opposition Jul. 27, 2016, 34 pp.
U.S. Appl. No. 11/363,867, filed Feb. 27, 2006, 70 pp.
U.S. Appl. No. 60/813,589, filed Dec. 29, 2005, 62 pp.
Ureter, https://en.wikipedia.org/wiki/Ureter, Jun. 2016, 6 pp.

* cited by examiner

SHAFTS WITH PRESSURE RELIEF IN CRYOTHERAPEUTIC CATHETERS AND ASSOCIATED DEVICES, SYSTEMS, AND METHODS

RELATED APPLICATIONS

This application is a continuation of and claims the benefit of U.S. patent application Ser. No. 13/458,120, filed Apr. 27, 2012, the disclosure of which is herein incorporated by reference in its entirety.

TECHNICAL FIELD

The present technology relates generally to cryotherapeutic devices (e.g., cryotherapeutic catheters including balloons configured to expand within the vasculature of a patient). In particular, several embodiments are directed to shafts with pressure relief in cryotherapeutic catheters and associated devices, systems, and methods.

BACKGROUND

Cryotherapy can be a useful treatment modality in a wide range of catheter-based interventional procedures. For example, cryotherapeutic cooling can be used to modulate nerves or affect other tissue proximate anatomical vessels and other lumens or cavities in the body. This can reduce undesirable neural activity to achieve therapeutic benefits. Catheter-based neuromodulation utilizing cryotherapy can be used, for example, to modulate nerves and thereby reduce pain, local sympathetic activity, systemic sympathetic activity, associated pathologies, and other conditions. Cryotherapy can also be used for ablating tumors, treating stenosis, and other applications. In some cryotherapeutic procedures, it can be useful to deliver cryotherapy via a balloon that can be expanded within an anatomical vessel or lumen. Such balloons can be operatively connected to extracorporeal support components (e.g., refrigerant supplies). As the applicability of cryotherapy for surgical intervention continues to expand, there is a need for innovation in the associated devices, systems, and methods (e.g., with respect to efficacy, efficiency, and/or reliability). Such innovation has the potential to further expand the role of cryotherapy as a tool for improving the health of patients.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology. Furthermore, components can be shown as transparent in certain views for clarity of illustration only and not to indicate that the illustrated component is necessarily transparent.

DETAILED DESCRIPTION

Figure 1:
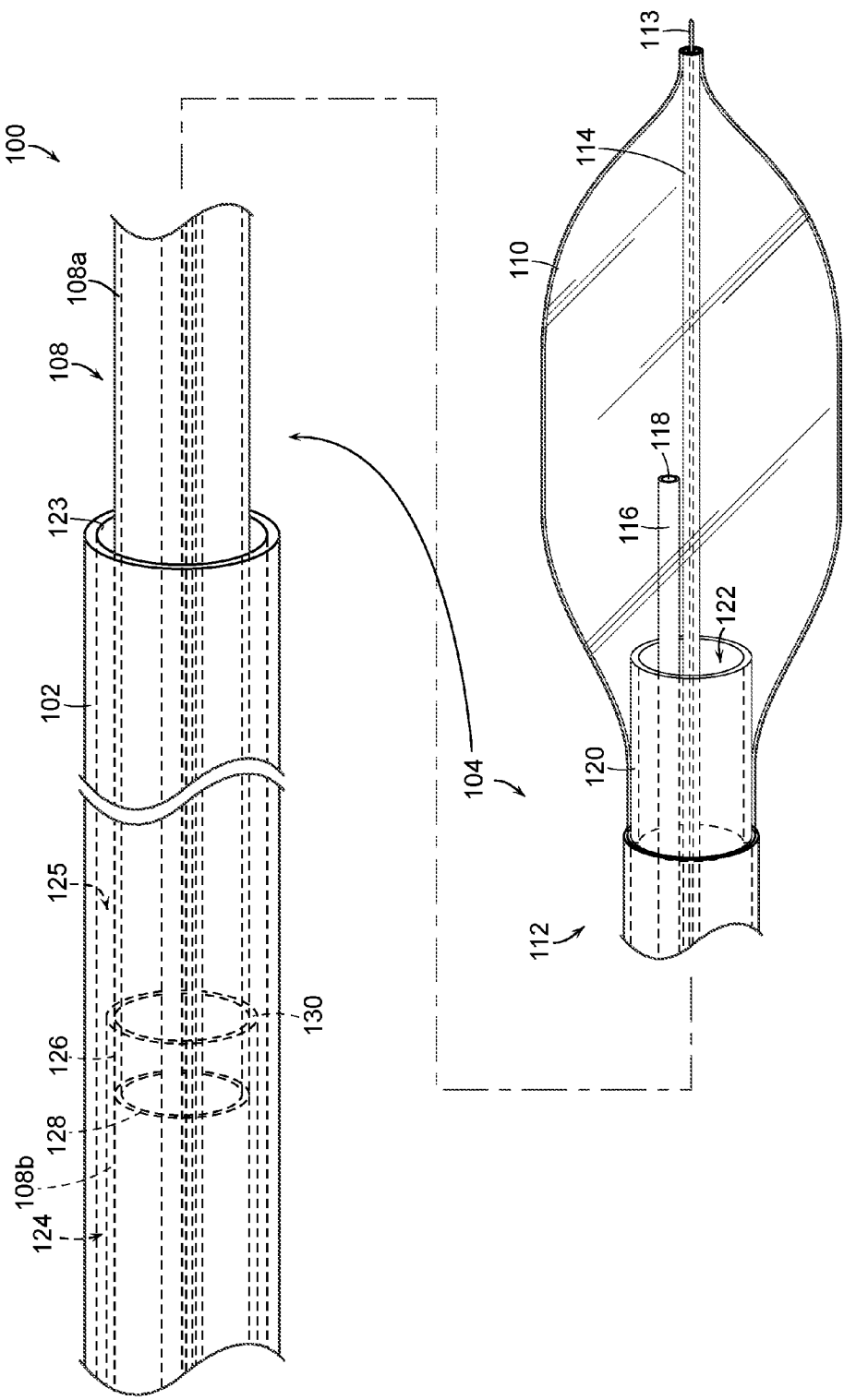
FIG. 1 is a perspective view illustrating a cryotherapeutic system configured in accordance with an embodiment of the present technology.

Specific details of several embodiments of the present technology are described herein with reference to FIGS. 1-6. Generally, unless the context indicates otherwise, the terms "distal" and "proximal" within this description reference a position relative to a refrigerant source, an operator, and/or an entry point into a patient. For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

In cryotherapeutic procedures, it can be desirable to apply cooling with high selectivity. Reducing cooling of non-targeted structures and tissue can enhance cooling efficiency and reduce complications. Although both high-pressure refrigerants and low-temperature refrigerants are potentially useful for cryotherapy, high-pressure refrigerants can be particularly well suited for delivering intense, targeted cooling to specific locations within the body, particularly in relatively small-diameter catheters. In many cases, the cooling potential of high-pressure refrigerants can be maintained more readily during transport through the catheter than low-temperature refrigerants. For example, a suitable strong-walled conduit can be used to convey a high-pressure refrigerant from an extracorporeal source to a delivery location at a distal end of a catheter with relatively little loss of cooling potential because the cooling action occurs upon expansion of the refrigerant at the distal end of the catheter. In contrast, as a low-temperature refrigerant moves along a catheter, it can be difficult to prevent the low-temperature refrigerant from absorbing heat from surrounding structures and tissue. Thermal insulation can be used to control such heat transfer to some extent, but adequate thermal insulation can be excessively bulky for use in modern, small-diameter catheters.

While advantageous in many respects, the use of high-pressure refrigerants can place certain constraints on catheter construction. For example, tubes configured to carry refrigerant supplies typically are constructed of metal, hard polymers (e.g., polyimides), or other suitable materials, and have wall thicknesses that allow the tubes to have pressure ratings higher than the pressures of the refrigerants they are configured to transport. After a high-pressure refrigerant undergoes expansion and cooling, its pressure can decrease dramatically. Accordingly, the catheter components that contain the refrigerant after expansion are not limited to strong-walled tubes and similar high-strength structures with pressure ratings higher than the pressures of the refrigerant before expansion. Furthermore, some cryotherapeutic procedures use balloons because they can be relatively compact when not inflated, thereby allowing for delivery through narrow anatomical vessels and lumens, and they can expand to generally conform to the size and shape of the treatment location. Balloons also can have relatively thin walls well suited for cryotherapeutic heat transfer. Thin-walled cryotherapy balloons, however, typically have relatively low pressure ratings. For example, cryotherapeutic balloons typically have pressure ratings well below the supply pressures of suitable high-pressure refrigerants.

In some embodiments of the present technology, a high-pressure refrigerant can be transported along at least a portion of the length of a catheter and then expanded to a relatively low-temperature and low-pressure state via the Joule-Thomson effect alone or in combination with evaporative cooling. The catheter can be constructed such that the expansion can occur at or near a balloon. With a sufficient pressure drop, cooling from near ambient temperatures to cryogenic temperatures can be achieved. Suitable refrigerants for pressurization and expansion in cryotherapeutic devices include, for example, $N_2O$, $CO_2$, and hydrofluorocarbons (e.g., Freon® refrigerant, R-410A, etc.), among others. To maintain a pressure drop within a balloon, an exhaust passage can be provided from the balloon to the atmosphere or to a low-pressure containment vessel. Since expanded refrigerant has a lower density than high-pressure refrigerant, the exhaust passage can have a greater free-passage area than a corresponding supply lumen. During normal operation, evacuation of expanded refrigerant via the exhaust passage maintains the pressure in the balloon sufficiently below the high pressures associated with the refrigerant supply.

If the exhaust passage is blocked while the supply of high-pressure refrigerant to the balloon continues, the pressure in the balloon can build up until it equilibrates with the pressure of the supply lumen. Similarly, the pressure in the balloon can approach a lower, but still elevated, pressure if the exhaust passage becomes partially blocked. The exhaust passage can be partially or fully blocked, for example, due to an operator error (e.g., if an extracorporeal line carrying the exhaust passage becomes kinked or compressed or if a backpressure control valve is closed unexpectedly). In these and other such scenarios, it is possible that the pressure within the balloon can exceed the pressure rating of the balloon, which can be related to the pressure at which the balloon is likely to fail. Balloon failures can include, for example, bursting, leakage, excessive expansion (e.g., beyond the elastic tolerances of surrounding anatomical vessels or lumens), or combinations thereof. In some cases, the pressure rating of a balloon can correspond to a burst pressure of the balloon. It is undesirable for balloons to fail during a procedure for a number of reasons.

Cryotherapeutic devices, systems, and methods configured in accordance with embodiments of the present technology can include one or more features useful for reducing the likelihood of balloon failures (e.g., associated with excessive pressure build up within a balloon due to partial or complete blockage of an exhaust passage). For example, some embodiments can include one or more features configured to release pressure automatically when the pressure within the balloon is about to reach, reaches, or exceeds a predetermined threshold relative to the pressure rating of the balloon or another pressure level. These features can prevent or at least mitigate undesirable balloon failure.

Figure 2:
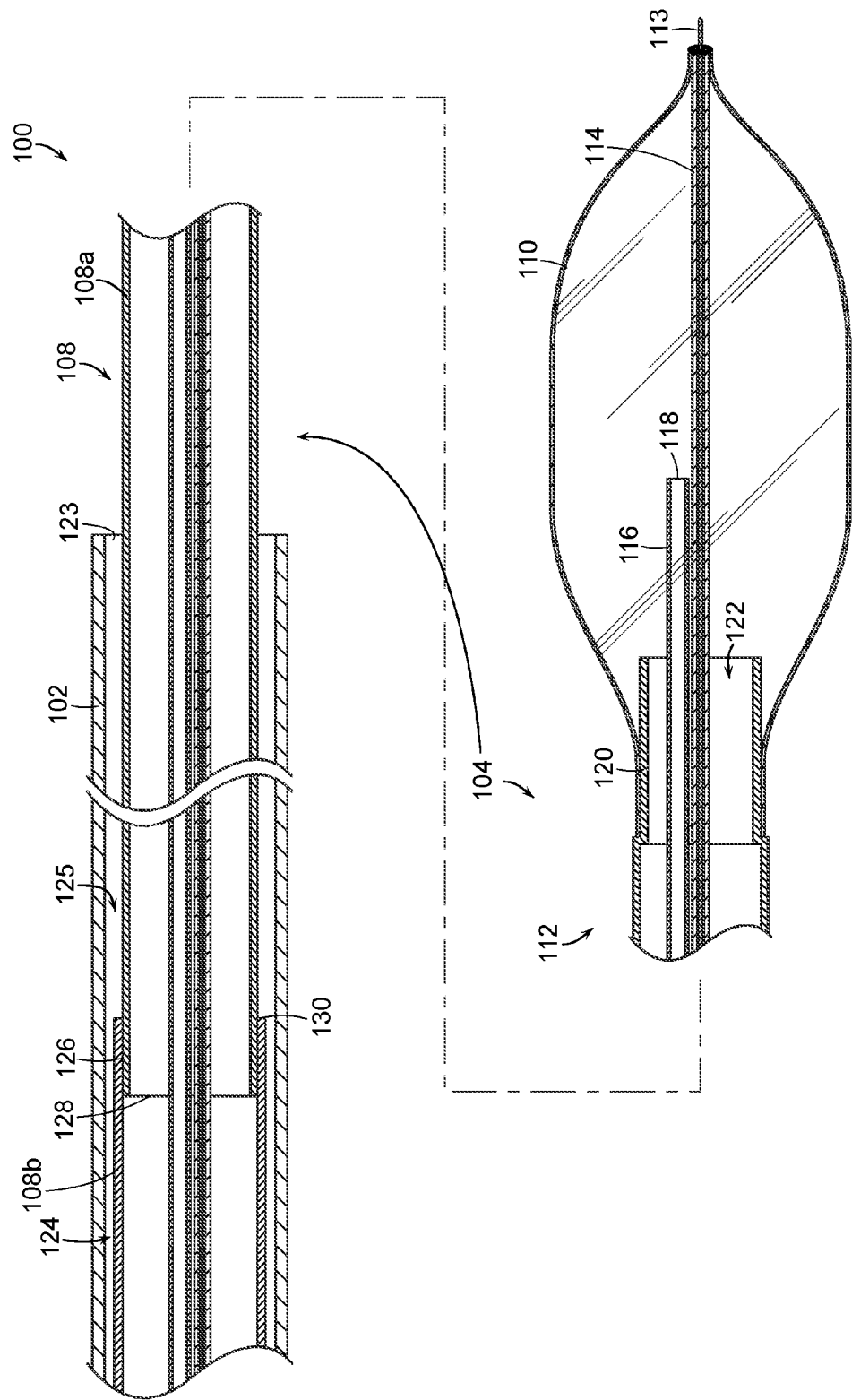
FIG. 2 is a cross-sectional view of the cryotherapeutic system of FIG. 1.

FIGS. 1-2 are, respectively, perspective and cross-sectional views illustrating a cryotherapeutic system 100 configured in accordance with an embodiment of the present technology. The cryotherapeutic system 100 can include a guide catheter 102 and a treatment catheter 104. As shown in FIGS. 1-2, the treatment catheter 104 can be configured for insertion into and through the guide catheter 102. In some embodiments, the guide catheter 102 can be 8 French or smaller (e.g., 7 French, 6 French, or smaller). The guide catheter 102 can include a guide passage 125 through which the treatment catheter 104 can be axially advanced and retracted. The cryotherapeutic system 100 can further include a guide wire 113 that can facilitate introducing the guide catheter 102 and/or the treatment catheter 104 to a desired location within the vessel or lumen. For example, during a treatment procedure, the guide wire 113 can be introduced percutaneously or through a natural anatomical orifice of the patient and advanced along a suitable catheterization path. Imaging (e.g., ultrasound, fluoroscopy, or another suitable imaging modality) can be used to aid in navigating the guide wire 113. Once in position, the guide catheter 102 can be advanced over the guide wire 113 and the treatment catheter 104 can subsequently be advanced through the guide passage 125 and over the guide wire 113. In other embodiments, the guide catheter 102 and the guide wire 113 can be introduced simultaneously. In still other embodiments, the guide catheter 102 and the treatment catheter 104 can be configured for use without a guide wire 113.

The treatment catheter 104 can include an elongated shaft 108 and a balloon 110 at a distal portion 112 of the shaft 108. The shaft 108 can be configured to locate the distal portion 112 within a vessel or lumen of a human patient. The treatment catheter 104 can further include a guide lumen 114 and a supply lumen 116 extending along at least a portion of the shaft 108, and the supply lumen 116 can have an orifice 118 within the balloon 110. The balloon 110 can extend from a stepped-down segment 120 of the distal portion 112 to an outer surface of the guide lumen 114. The supply lumen 116 can be configured to supply high-pressure refrigerant to the balloon 110 via the orifice 118. The high-pressure refrigerant can change phase from a liquid to a gas within the balloon 110, which can expand and cool the balloon 110. The treatment catheter 104 can also have an exhaust passage 122 extending proximally from the balloon 110 along at least a portion of the shaft 108 (e.g., around the guide lumen 114 and the supply lumen 116) to the atmosphere or an extracorporeal containment vessel (not shown). During operation, refrigerant flows to the balloon 110 through the supply lumen 116 and out of the balloon 110 via the exhaust passage 122. The exhaust passage 122 can have a greater free-passage area than the supply lumen 116 to accommodate the lower density of expanded refrigerant relative to the high-pressure refrigerant within the supply lumen 116.

As shown in FIGS. 1-2, the treatment catheter 104 can be configured to extend beyond a distal opening 123 of the guide catheter 102. For example, during a treatment procedure, at least a portion of the distal portion 112 of the shaft 108 can extend beyond the distal opening 123 to locate the balloon 110 at a desired treatment location spaced apart from the distal opening 123. When the balloon 110 is outside the guide passage 125 of the guide catheter 102, the balloon 110 can radially expand to a diameter greater than the diameter of the guide passage 125.

The shaft 108 can further include a pressure-relief portion 124 located proximally relative to the distal portion 112. In some embodiments, the distal portion 112 can extend along an entire length of the treatment catheter 104 between the pressure-relief portion 124 and the balloon 110. In other embodiments, the shaft 108 can include an intermediate portion (not shown) between the pressure-relief portion 124 and the distal portion 112. The pressure-relief portion 124 can be configured to release refrigerant from the exhaust passage 122 (e.g., to a space in the guide passage 125 between the treatment catheter 104 and the guide catheter 102) when a pressure of refrigerant in at least a portion of the exhaust passage 122 (e.g., a portion at or near the pressure-relief portion 124), the balloon 110, or both exceeds a threshold pressure. The threshold pressure, for example, can be less than a pressure rating of the balloon 110 (e.g., a pressure rating corresponding to a burst pressure of the balloon 110).

As shown in FIGS. 1-2, the distal portion 112 can include a first segment 108a of the shaft 108 and the pressure-relief portion 124 can include a second segment 108b of the shaft 108. The first and second segments 108a-b can be attached to one another at a lap joint 126 (e.g., via compression, adhesive bonding, thermal welding, or another suitable attachment mechanism). For example, a proximal end 128 of the first segment 108a can be within the second segment 108b at the lap joint 126. In other embodiments, a distal end 130 of the second segment 108b can be within the first segment 108a at the lap joint 126. As shown in FIGS. 1-2, the diameter of the first segment 108a can be less than the diameter of the second segment 108b. Correspondingly, the free-passage area of the first segment 108a can be less than the free-passage area of the second segment 108b. The free-passage area of the first segment 108a can define the free-passage area of the overall exhaust passage 122. Since refrigerant can warm and expand as it travels proximally along the exhaust passage 122, the smaller free-passage area of the first segment 108a relative to the free-passage area of the second segment 108b can have little or no effect on flow through the exhaust passage 122.

Figure 3:
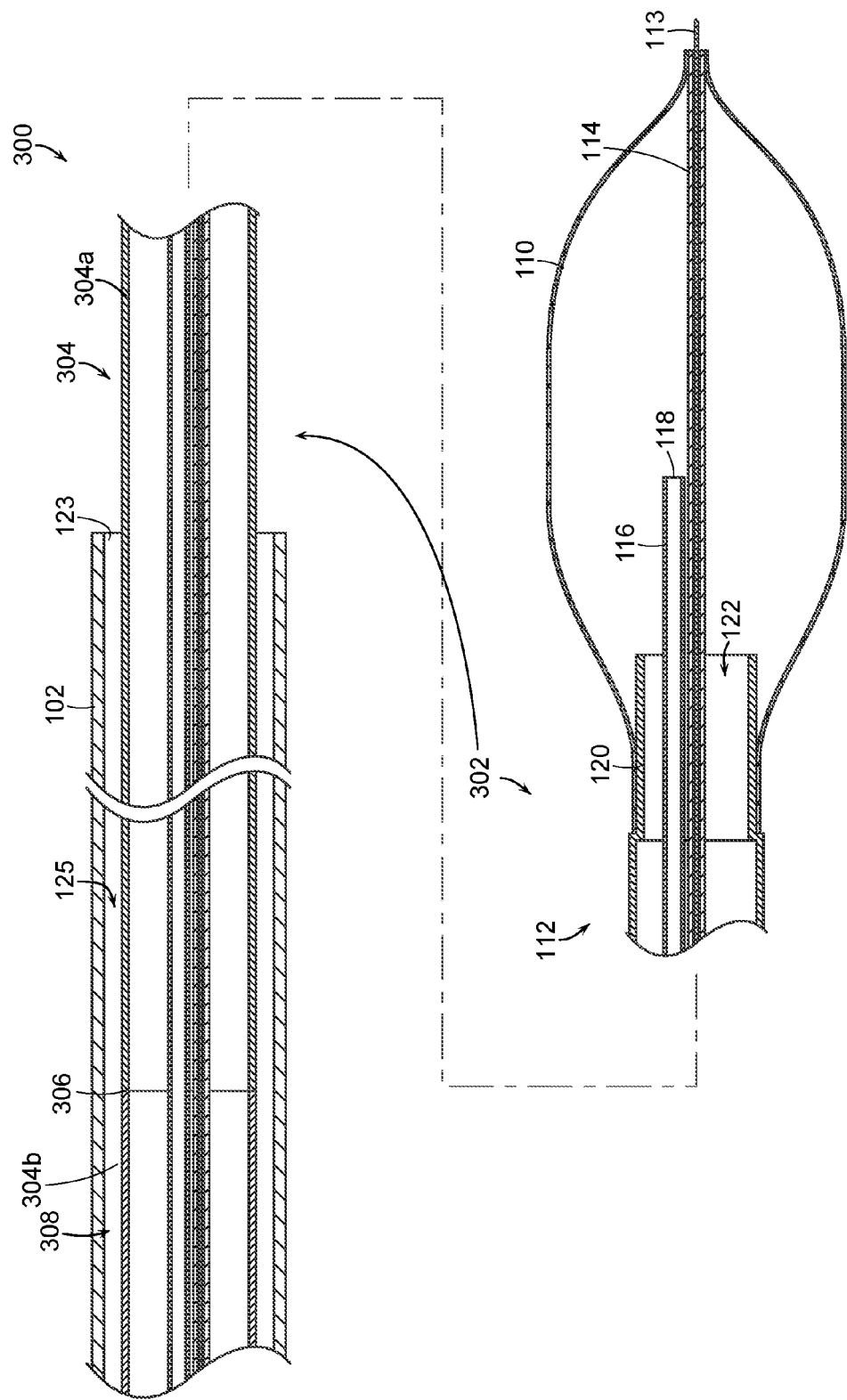
FIGS. 3-6 are cross-sectional views illustrating cryotherapeutic systems configured in accordance with additional embodiments of the present technology.

The lap joint 126 can provide a particularly strong connection between the first and second segments 108a-b, but other connections can also be used. For example, FIG. 3 is a cross-sectional view illustrating a cryotherapeutic system 300 configured in accordance with an embodiment of the present technology that is similar to the cryotherapeutic system 100 shown in FIGS. 1-2. The cryotherapeutic system 300 can include a treatment catheter 302 having an elongated shaft 304 with a distal first segment 304a connected to a proximal second segment 304b by a butt joint 306 in place of the lap joint 126 shown in FIGS. 1-2. The shaft 304 can include a pressure-relief portion 308 defined by the second segment 304b which has a diameter at least approximately equal to the diameter of the first segment 304a. The first segment 304a can be a component of the distal portion 112. The butt joint 306 can be formed by adhesive bonding, thermal welding, or another suitable attachment mechanism between the first and second segments 304a-b.

With reference to FIGS. 1-3, in some embodiments, the distal portion 112 can have a wall strength (e.g., yield strength or ultimate tensile strength) greater than a wall strength of the pressure-relief portion 124, 308. For example, the first segment 108a, 304a can have a wall strength greater than a wall strength of the second segment 108b, 304b. The wall strength of all or a portion of the pressure-relief portion 124, 308 or the second segment 108b, 304b, for example, can be less than about 80% (e.g., less than about 60% or less than about 40%) of that of the distal portion 112 or the first segment 108a, 304a. Different constructions and/or compositions can cause the different wall strengths. For example, the pressure-relief portion 124, 308 or the second segment 108b, 304b can include walls that are thinner and/or made of weaker materials than walls of the distal portion 112 or the first segment 108a, 304a. In some embodiments, the pressure-relief portion 124, 308 or the second segment 108b, 304b can be made of polyamide and the distal portion 112 or the first segment 108a, 304a can be made of polyimide. In other embodiments, the pressure-relief portion 124, 308 or the second segment 108b, 304b can be made of a polyimide at a first thickness and the distal portion 112 or the first segment 108a, 304a can be made of a polyimide at a second thickness greater than the first thickness. When the pressure-relief portion 124, 308 or the second segment 108b, 304b is braided, the braid pattern or density can be selected to cause a wall strength lower than that of the distal portion 112 or the first segment 108a, 304a. Similarly, when the pressure-relief portion 124, 308 or the second segment 108b, 304b includes multiple layers, the number of layers can be selected to cause a wall strength lower than that of the distal portion 112 or the first segment 108a, 304a. A variety of other suitable materials and configurations are also possible.

The wall strength of the pressure-relief portion 124, 308 or the second segment 108b, 304b can be selected to cause the pressure-relief portion 124, 308 or the second segment 108b, 304b to rupture at about the threshold pressure. Accordingly, the pressure-relief portion 124, 308 or the second segment 108b, 304b can be sacrificial and/or otherwise configured to fail before the balloon 110 fails during a malfunction in which the pressure in the balloon 110 increases unexpectedly. Failure of the pressure-relief portion 124, 308 or the second segment 108b, 304b can allow refrigerant to quickly flow into the space in the guide passage 125 between the shaft 108 and the guide catheter 102. At least a portion of the refrigerant in the space can then move proximally to a proximal opening (not shown) of the guide catheter 102. In some embodiments, the pressure-relief portion 124, 308 or the second segment 108b, 304b can be configured to rupture relatively rapidly. For example, the pressure-relief portion 124, 308 or the second segment 108b, 304b can include a relatively brittle material, such as a material having an elongation at break less than about 50% (e.g., less than about 30% or less than about 20%). In other embodiments, the pressure-relief portion 124, 308 or the second segment 108b, 304b can be configured to rupture more slowly.

Figure 4:
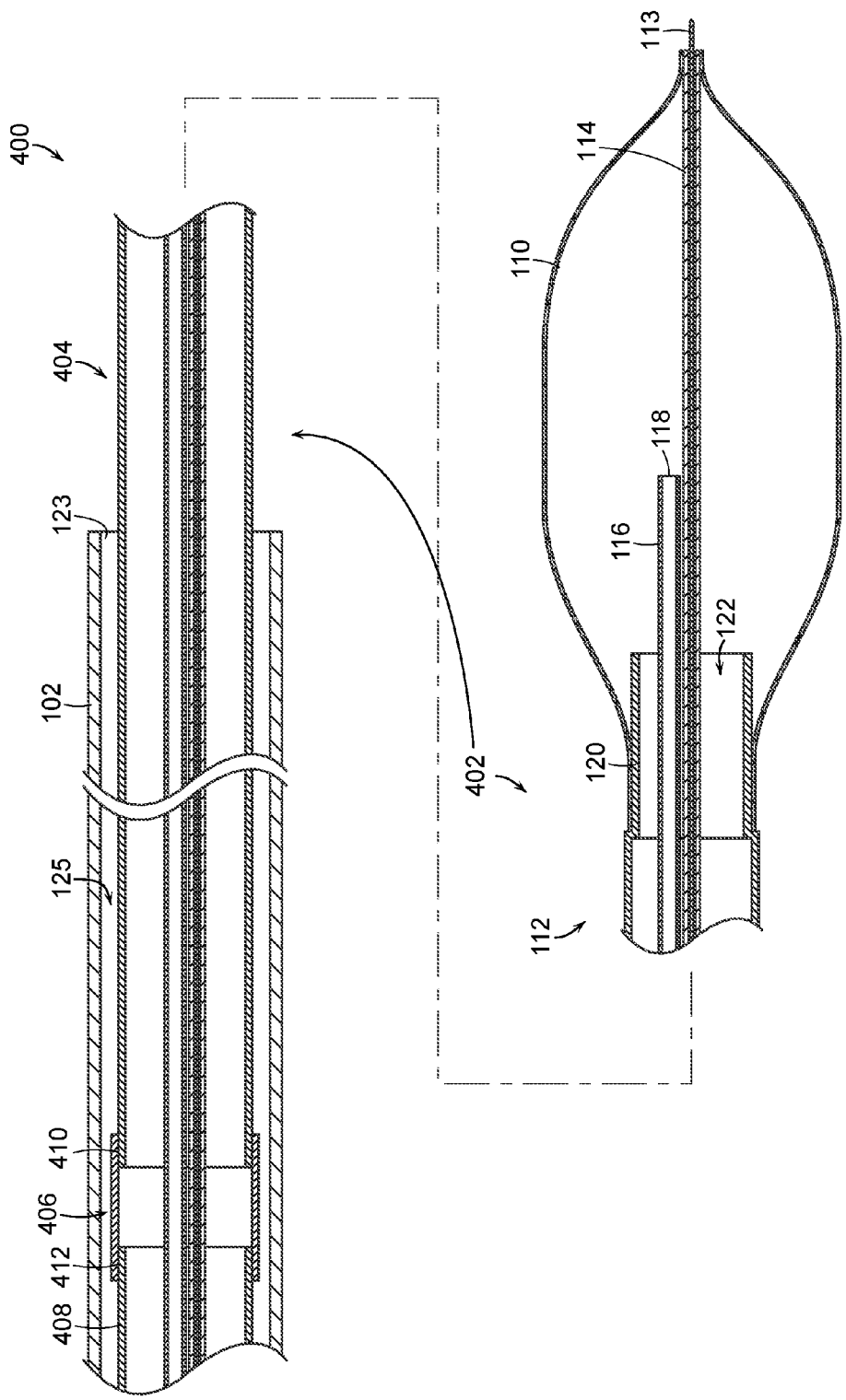

In the cryotherapeutic systems 100, 300 shown in FIGS. 1-3, it may be difficult to predict where the pressure-relief portion 124, 308 or the second segment 108b, 304a will sacrificially release the pressure along the exhaust passage 122. As such, it may be desirable to control the release of refrigerant at specific locations along the device. FIG. 4 is a cross-sectional view illustrating one example of a cryotherapeutic system 400 configured in accordance with another embodiment of the present technology that includes a treatment catheter 402 having a shaft 404 with a relatively short pressure-relief portion 406. The shaft 404 can further include a proximal portion 408 proximal to the pressure-relief portion 406, a first lap joint 410 between the distal portion 112 and the pressure-relief portion 406, and a second lap joint 412 between the pressure-relief portion 406 and the proximal portion 408. In other embodiments, the first and second lap joints 410, 412 can be replaced with butt joints or other suitable connections. The pressure-relief portion 406 can have a lower pressure rating than the distal portion 112, the proximal portion 408, and the balloon 110 such that the pressure-relief portion 406 preferentially fails at a specific location along the device.

Figure 5:
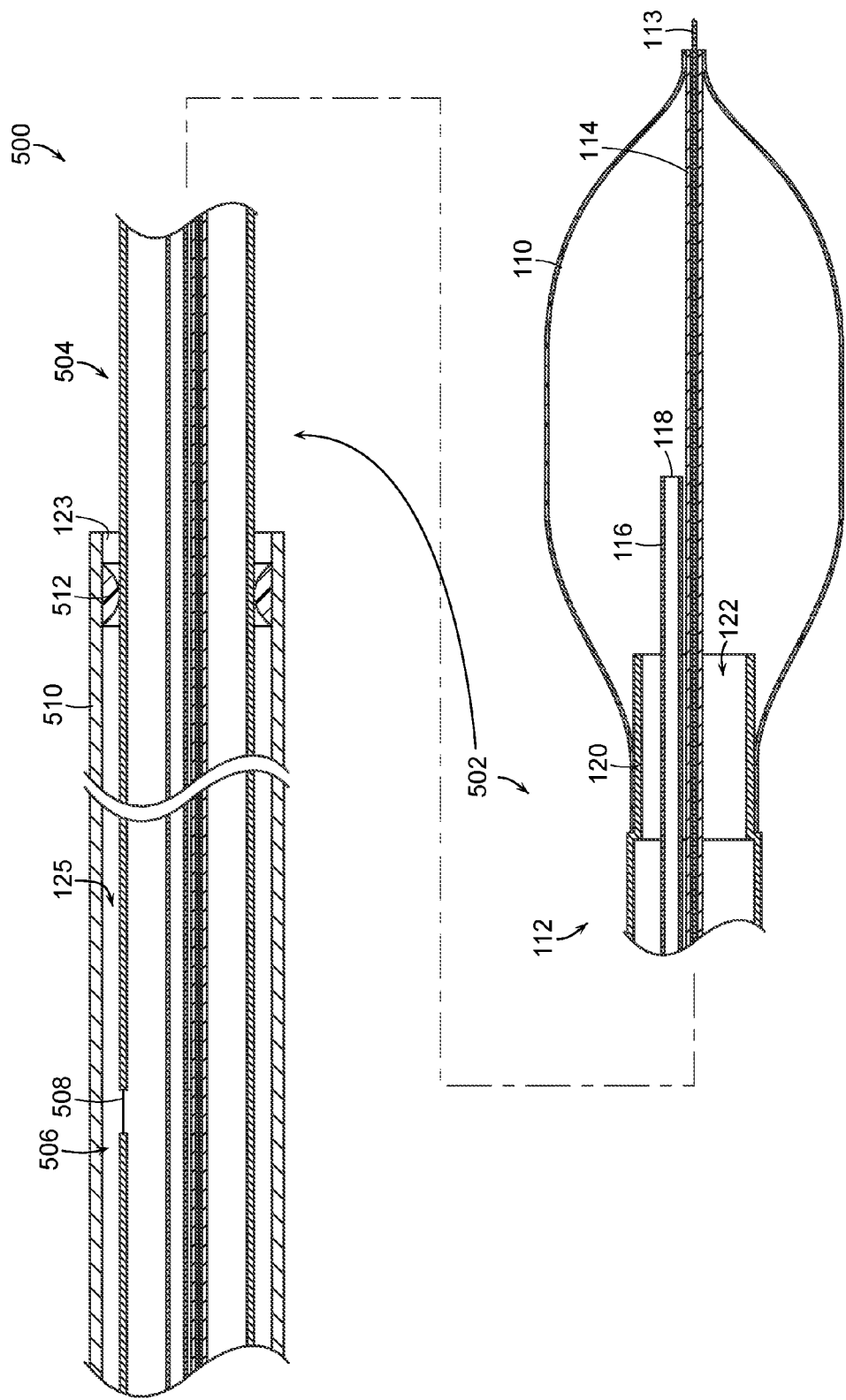

FIG. 5 is a cross-sectional view illustrating a cryotherapeutic system 500 configured in accordance with an embodiment of the present technology having another pressure-relief configuration. The cryotherapeutic system 500 can include a treatment catheter 502 having a shaft 504 with a pressure-relief portion 506 including a rupture element 508. In the embodiment shown in FIG. 5, the rupture element 508 does not extend around the entire circumference of the shaft 504. In other embodiments, the rupture element 508 can be annular and can extend around the entire circumference of the shaft 504. The rupture element 508 can include a membrane (e.g., embedded within a wall of the pressure-relief portion 506), a weakened (e.g., scored and/or thinned) portion of a wall of the pressure-relief portion 506, or another suitable structure configured to break predictably in response to pressure. The rupture element 508, for example, can be configured to rupture in response to a pressure in an adjacent portion of the exhaust passage 122 that is near or exceeds the threshold pressure. The size of the rupture element 508 can be selected to control the rate at which refrigerant is released from the exhaust passage 122 into the space in the guide passage 125.

With reference to FIGS. 1-5, the locations of the pressure-relief portions 124, 308, 406, 506 and/or portions thereof (e.g., the first segments 108a, 304a of the pressure-relief portions 124, 308 and the rupture element 508 of the pressure-relief portion 506) can be selected to control the locations where refrigerant is released into the space in the guide passage 125. In some embodiments, the release locations can be outside vessels or lumens of patients during treatment procedures. For example, such release locations can be proximal relative to entry points into the vessels or lumens and, in some cases, proximal to proximal openings of corresponding guide catheters 102. Such release locations can reduce the possibility that the refrigerant will be released into the vessels or lumens via the distal openings 123 of the guide catheters 102. Locations closer to the balloons 110, however, can be useful to decrease pressure differential and/or delay between the release point along the exhaust passages 122 and the balloon 110. This can improve the responsiveness of the pressure-relief portions 124, 308, 406, 506 to rapid increases in pressure within the balloon 110. Furthermore, in some cases, the pressure-relief portions 124, 308, 406, 506 may have limited effectiveness when blockages of the corresponding exhaust passages occur between the pressure-relief portions 124, 308, 406, 506 and the balloon 110. Decreasing the distance between the pressure-relief portions 124, 308, 406, 506 and the balloon 110 can decrease the likelihood of such blockages. In some embodiments, the pressure-relief portions 124, 308, 406, 506 can be proximally spaced apart from the balloon 110 such that the pressure-relief portions 124, 308, 406, 506 are just within the corresponding guide passage 125.

With reference again to FIG. 5, the cryotherapeutic system 500 can also include a guide catheter 510 having a flow restrictor 512 around a perimeter of the guide passage 125. In other embodiments, the treatment catheter 502 can include the flow restrictor 512 at a position distal to the pressure-relief portion 506. The flow restrictor 512 can be configured to reduce or prevent distal flow of released refrigerant within the guide passage 125 through the distal opening 123 and into a vessel or lumen of a patient. Instead, the path of least resistance for the released refrigerant can extend proximally through the guide passage 125 to the proximal opening of the guide catheter 510 outside the vessel or lumen. In some embodiments, the flow restrictor 512 can be at least partially annular and/or compressible and configured to conform to the shaft 504. Furthermore, the flow restrictor 512 can be configured to reduce or prevent proximal blood flow within the guide catheter 510 in addition to reducing or preventing distal refrigerant flow. Other embodiments can include different features for reducing or preventing distal flow of released refrigerant. For example, the cryotherapeutic system 200 shown in FIG. 2 can be modified such that the second segment 108b is within the first segment 108a at the lap joint 126 and the distal portion 112 has a larger diameter than the pressure-relief portion 124. This can reduce the space in the guide passage 125 around the distal portion 112 and thereby encourage flow of released refrigerant in a proximal direction. In some embodiments, refrigerant released into a vessel or lumen of a patient through the distal opening 123 can be less problematic than refrigerant release resulting from a balloon failure, thereby reducing the usefulness of the flow restrictor 512. Furthermore, the pressure-relief portion 506 can be located closer to the proximal opening of the guide catheter 510 than to the distal opening 123 of the guide catheter 510, which can delay or prevent refrigerant release into a vessel or lumen of a patient through the distal opening 123.

Figure 6:
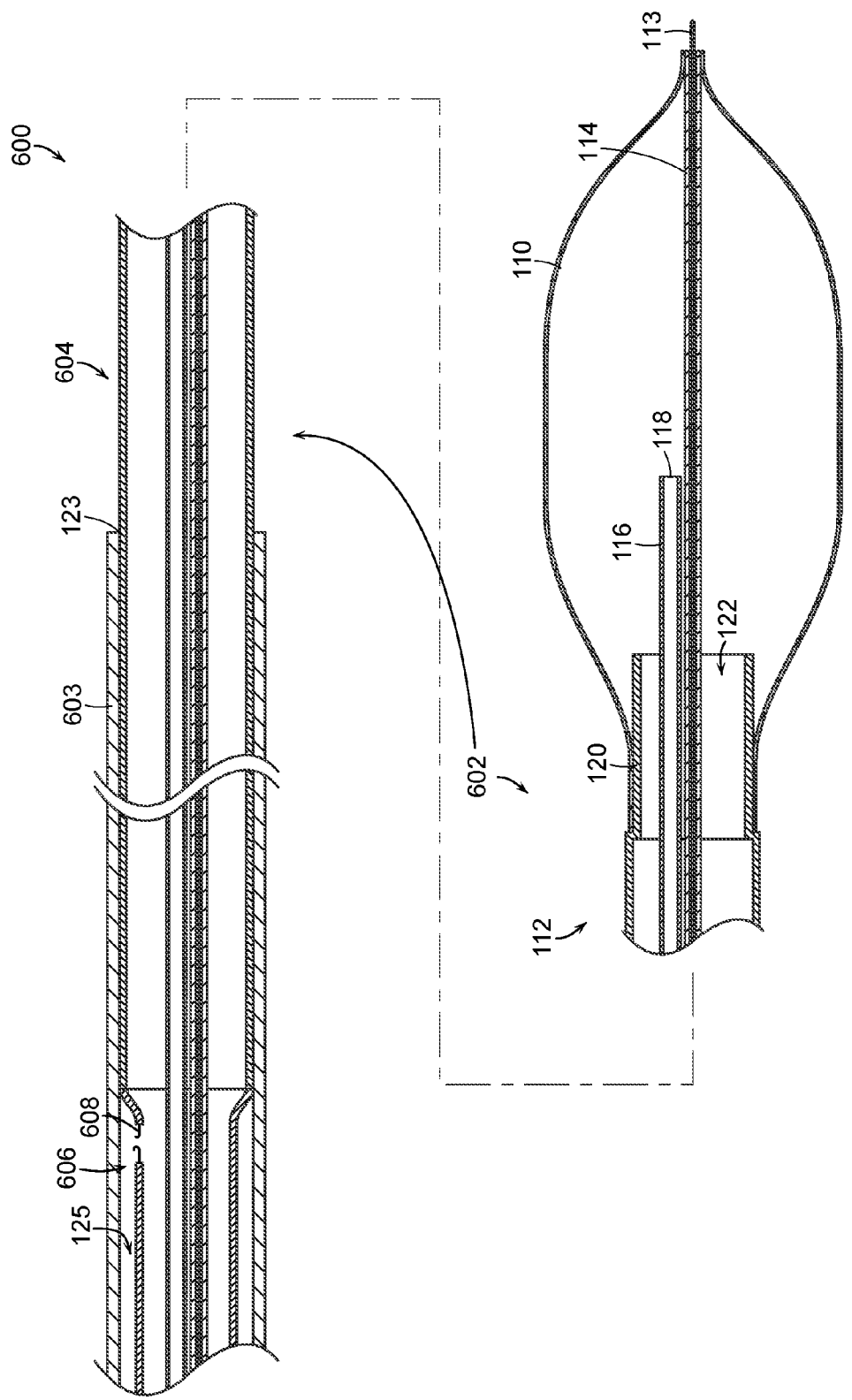

In some embodiments the diameter of the treatment catheter 502 and/or the diameter of the guide catheter 510 can be selected to size the space therebetween in the guide passage 125. For example, a difference between the outer diameter of the shaft 504 at and the inner diameter of the guide passage 125 can be greater than about 0.2 mm (e.g., greater than about 0.3 mm or greater than about 0.4 mm) along at least about 100 cm of the shaft 504 extending proximally from the pressure-relief portion 506. In some cases, however, it can be useful to reduce the size of the space in the guide passage 125 in favor of increasing the size of the shaft 504. For example, larger-diameter shafts can support greater cooling. FIG. 6 is a cross-sectional view illustrating a cryotherapeutic system 600 configured in accordance with an embodiment of the present technology and including a treatment catheter 602 and a guide catheter 603. The treatment catheter 602 can include a shaft 604 having a pressure-relief portion 606 with a rupture element 608. The guide catheter 603 can be smaller and/or the shaft 604 can be larger than the embodiments shown in FIGS. 1-5 to provide a relatively close fit that restricts the distal flow of refrigerant along the space in the guide passage 125.

The pressure-relief portion 606 and portions of the shaft 604 proximal to the pressure-relief portion 606 can have a smaller diameter than the distal portion 112 such that there is more space between the proximal portion of the shaft 604 and the guide catheter 602. This can facilitate the proximal flow of refrigerant along the space within the guide passage 125 (e.g., from a release location proximate the rupture element 608 along a generally continuous path to a proximal opening of the guide catheter 603). The path, for example, can be greater than about 100 cm (e.g., greater than about 200 cm or greater than about 300 cm) in length and can extend proximally from the rupture element 608. In some embodiments, the pressure-relief portion 606 can be configured to deform from a first state (not shown) in which the pressure-relief portion 606 has a diameter similar to the diameter of the distal portion 112 to a second state (shown in FIG. 6) in which the rupture element 608 is ruptured and the pressure-relief portion 606 deforms inwardly. The pressure-relief portion 606 can deform, for example, in response to pressure within the space in the guide passage 125 exceeding a threshold pressure. As shown in FIG. 6, in some embodiments, the pressure-relief portion 606 can deform generally evenly. In other embodiments, the pressure-relief portion 606 and portions of the shaft 604 proximal to the pressure-relief portion 606 can be configured to selectively deform (e.g., along a channel). Deforming can occur, for example, as a result of reversible or irreversible compression or expansion of at least a portion of a wall of the shaft 604. For example, the shaft 604 can be at least partially elastic, folded, articulated, or otherwise configured to expand or contract in response to pressure within the guide passage 125. In other embodiments, the shaft 604 can have general or local wall strength sufficiently low to allow the shaft 604 to deform inwardly in response to pressure within the guide passage 125.

In some embodiments, the disclosed pressure-relief features can be redundant to other features intended to prevent balloon failures. For example, the cryotherapeutic systems shown in FIGS. 1-6 can include one or more pressure sensors (not shown) configured to monitor pressures within the balloon 110 and controllers (not shown) configured to stop refrigerant flow to the balloon 110 if the monitored pressures increase above threshold pressures. In other embodiments, the disclosed pressure-relief features can take the place of pressure monitoring. Furthermore, reducing the likelihood of balloon failure can allow for greater freedom in balloon constructions and compositions. In some embodiments, the balloon 110 can have a pressure rating less than about 400% (e.g., less than about 300% or less than about 200%) of a steady-state pressure within the balloon 110 during normal operation. This can facilitate, for example, the use of balloons 110 having thinner walls and greater elasticity.

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while stages may be presented in a given order, alternative embodiments may perform stages in a different order. The various embodiments described herein and elements thereof may also be combined to provide further embodiments. In some cases, well-known structures and functions have not been shown or described in detail to avoid unnecessarily obscuring the description of embodiments of the present technology.

Where the context permits, singular or plural terms may also include the plural or singular terms, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout the disclosure to mean including at least the recited feature(s) such that any greater number of the same feature(s) and/or additional types of other features are not precluded. It will also be appreciated that various modifications may be made to the described embodiments without deviating from the present technology. Further, while advantages associated with certain embodiments of the present technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

We claim:

1. A cryotherapeutic catheter comprising:
   an elongate shaft having a distal end portion, a pressure-relief portion proximal to the distal end portion, and a collapsible portion proximal to the pressure-relief portion, wherein the shaft is configured to move longitudinally within a guide passage defined by a tubular guide catheter, wherein the distal end portion of the shaft is configured to sealingly contact the guide catheter and thereby occlude an annular gap between the shaft and the guide catheter;
   a supply lumen carried by the shaft;
   an exhaust passage carried by the shaft; and
   a balloon at the distal end portion of the shaft wherein the balloon is configured to receive refrigerant from the supply lumen and to exhaust refrigerant to the exhaust passage,
   wherein the pressure-relief portion of the shaft is configured to rupture and thereby release refrigerant therethrough from the exhaust passage when a pressure of refrigerant within the exhaust passage exceeds a threshold pressure less than a pressure rating of the balloon, and
   wherein the collapsible portion of the shaft configured to collapse in response to pressure from refrigerant released from the exhaust passage via the pressure-relief portion of the shaft.

2. The cryotherapeutic catheter of claim 1 wherein the distal end portion of the shaft includes an annular flow restrictor configured to sealingly contact the guide catheter.

3. The cryotherapeutic catheter of claim 2 wherein the flow restrictor is compressible.

4. The cryotherapeutic catheter of claim 1, wherein
   the shaft has a first wall strength at its distal end portion;
   the shaft has a second wall strength at its pressure-relief portion; and
   the second wall strength is less than the first wall strength.

5. The cryotherapeutic catheter of claim 4, wherein the second wall strength is selected to cause the pressure-relief portion of the shaft to rupture when the pressure of refrigerant within the exhaust passage exceeds the threshold pressure.

6. The cryotherapeutic catheter of claim 4, wherein the shaft includes a butt joint between its distal end portion and its pressure-relief portion.

7. The cryotherapeutic catheter of claim 4, wherein the shaft includes a lap joint between its distal end portion and its pressure-relief portion.

8. The cryotherapeutic catheter of claim 4 wherein the second wall strength is less than 80% of the first wall strength.

9. The cryotherapeutic catheter of claim 1 wherein the pressure-relief portion of the shaft includes a membrane configured to rupture when the pressure of refrigerant within the exhaust passage exceeds the threshold pressure.

10. The cryotherapeutic catheter of claim 1 wherein the pressure-relief portion of the shaft is a scored portion of a wall of the shaft.

11. The cryotherapeutic catheter of claim 1 wherein the shaft has a smaller diameter at its pressure-relief portion than at its distal end portion.

12. The cryotherapeutic catheter of claim 1 wherein the shaft has a smaller diameter proximal to its pressure-relief portion than at its distal end portion.

13. The cryotherapeutic catheter of claim 1 wherein the collapsible portion of the shaft has a length of at least 100 cm.

14. The cryotherapeutic catheter of claim 1, wherein the pressure rating of the balloon corresponds to a burst pressure of the balloon.

15. The cryotherapeutic catheter of claim 1, wherein the shaft is configured to move longitudinally within a guide passage defined by a tubular guide catheter that is 8 French or smaller.

* * * * *